United States Patent
Schuster et al.

(10) Patent No.: US 12,357,154 B2
(45) Date of Patent: *Jul. 15, 2025

(54) SHORT WAVE INFRARED IMAGING ENDOSCOPY

(71) Applicant: The Johns Hopkins University, Baltimore, MD (US)

(72) Inventors: Paul R. Schuster, Baltimore, MD (US); Chad N. Weiler, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 480 days.

This patent is subject to a terminal disclaimer.

(21) Appl. No.: 17/317,495

(22) Filed: May 11, 2021

(65) Prior Publication Data

US 2021/0321866 A1 Oct. 21, 2021

Related U.S. Application Data

(63) Continuation-in-part of application No. 16/254,686, filed on Jan. 23, 2019, now Pat. No. 11,693,229.

(60) Provisional application No. 62/647,007, filed on Mar. 23, 2018.

(51) Int. Cl.
*A61B 1/00* (2006.01)
*A61B 1/005* (2006.01)
(Continued)

(52) U.S. Cl.
CPC ...... *A61B 1/00096* (2013.01); *A61B 1/00009* (2013.01); *A61B 1/00043* (2013.01);
(Continued)

(58) Field of Classification Search
CPC . A61B 1/00096; A61B 1/046; A61B 1/00009; A61B 1/00043; A61B 1/00188;
(Continued)

(56) References Cited

U.S. PATENT DOCUMENTS

| 9,897,762 B2 | 2/2018 | Reed et al. | |
| 2007/0171524 A1* | 7/2007 | Steinthal | G02B 7/06 |
| | | | 359/466 |

(Continued)

FOREIGN PATENT DOCUMENTS

DE 102014115738 A1 * 5/2016 ............... A61B 1/05

OTHER PUBLICATIONS

F. Akhoundi, et al., "Compact Fiber-Based Multi-Photon Endoscope Working at 1700nm," Biomedical Optics Express, vol. 9, No. 5, May 1, 2018, pp. 2326-2335.

(Continued)

*Primary Examiner* — Thai Q Tran
*Assistant Examiner* — Nienru Yang
(74) *Attorney, Agent, or Firm* — Todd R. Farnsworth

(57) ABSTRACT

An example imaging apparatus that can operate at shortwave infrared (SWIR) wavelengths are provided. An example imaging apparatus may include a flexible elongate member having a distal end and proximal end. The flexible elongate member may include a shortwave infrared (SWIR) imaging sensor disposed at the distal end and a lens optically coupled to the SWIR imaging sensor and disposed at the distal end of the flexible elongate member, the lens configured to focus light energy at the SWIR wavelength onto the SWIR imaging sensor. The member may also include an illumination source configured to provide light energy at the SWIR wavelength at the distal end of the flexible elongate member for output to illuminate an object.

14 Claims, 10 Drawing Sheets

(51) Int. Cl.
*A61B 1/04* (2006.01)
*A61B 1/05* (2006.01)
*A61B 1/06* (2006.01)

(52) U.S. Cl.
CPC ........ *A61B 1/00188* (2013.01); *A61B 1/0052* (2013.01); *A61B 1/0057* (2013.01); *A61B 1/046* (2022.02); *A61B 1/05* (2013.01); *A61B 1/063* (2013.01); *A61B 1/0638* (2013.01); *A61B 1/0646* (2013.01); *A61B 1/0669* (2013.01); *A61B 1/0676* (2013.01)

(58) Field of Classification Search
CPC ....... A61B 1/0052; A61B 1/0057; A61B 1/05; A61B 1/063; A61B 1/0638; A61B 1/0646; A61B 1/0669; A61B 1/0676
USPC ........................................................ 600/473
See application file for complete search history.

(56) References Cited

U.S. PATENT DOCUMENTS

| | | | | |
|---|---|---|---|---|
| 2011/0120458 A1* | 5/2011 | Schwartz | ............... | A61B 1/267 128/200.26 |
| 2013/0250618 A1* | 9/2013 | Nichol | ................ | G02B 6/0076 362/621 |
| 2016/0076936 A1* | 3/2016 | Schoch | ................ | G01J 1/4228 250/349 |
| 2017/0231477 A1* | 8/2017 | del Nido | ............ | A61B 17/3423 600/104 |
| 2018/0017227 A1 | 1/2018 | Greene et al. | | |

OTHER PUBLICATIONS

J. Carr, et al., "Shortwave Infrared Fluorescence Imaging with the Clinically Approved Near-Infrared Dye Indocyanine Green," Proceedings of the National Academy of Sciences (PNAS) Apr. 2018, 115 (17) 4465-4470.

Z. Starosolski, et al., "Indocyanine Green Fluorescence in Second Near-Infrared (NIR-II) Window," PLoS ONE 12 (11), Nov. 9, 2017, pp. 1-14.

H.A.C. Wood, et al., "High-Resolution Air-Clad Imaging Fibers," Optics Letters, vol. 43, No. 21, Nov. 1, 2018, pp. 5311-5314.

Schott; Medical—Leached Fiber Bundle | Schott North America; available at: https://www.us.schott.com/lightingimaging/english/medical/medical-products/transmitting-images_leached-image-bundle.html; last accessed May 10, 2019.

* cited by examiner

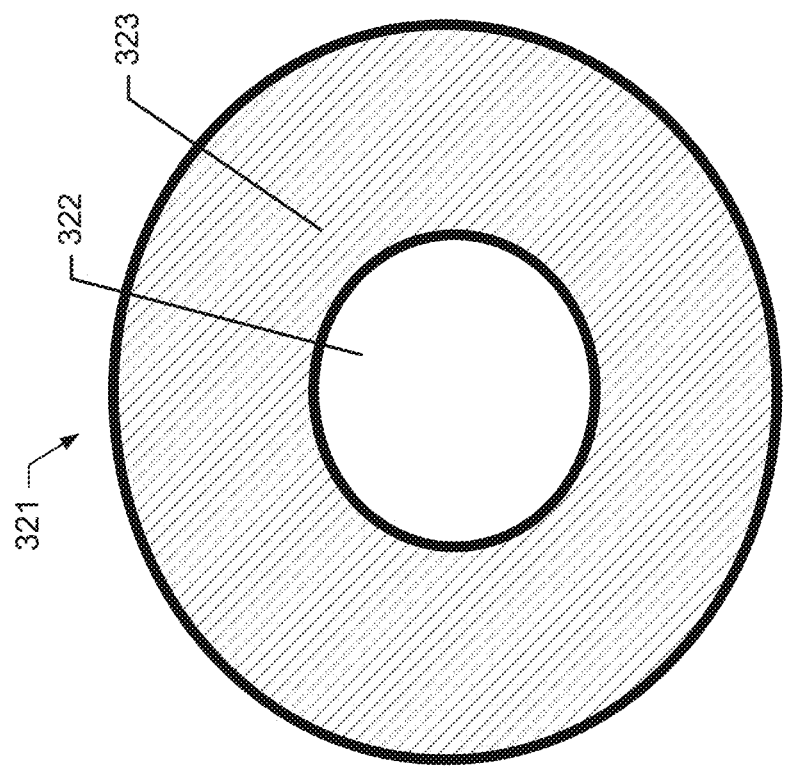
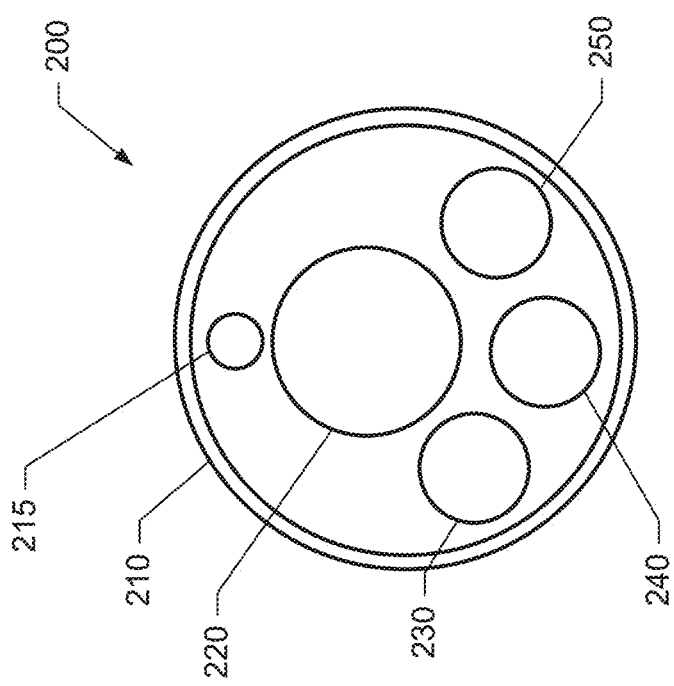
FIG. 3A
FIG. 2

SHORT WAVE INFRARED IMAGING ENDOSCOPY

CROSS-REFERENCE TO RELATED APPLICATIONS

This application is a continuation-in-part of prior application Ser. No. 16/254,686, filed Jan. 23, 2019, which claims the benefit of U.S. Provisional Application No. 62/647,007 filed on Mar. 23, 2018, the entire contents of both are hereby incorporated herein by reference.

STATEMENT OF GOVERNMENTAL INTEREST

This invention was made with U.S. Government support. The government has certain rights in the invention.

TECHNICAL FIELD

Example embodiments generally relate to imaging systems and, in particular, relate to imaging systems that include fiber optic bundles to support imaging applications.

BACKGROUND

Imaging systems have proven to be extremely useful in many applications. In some instances, there is a need for an imaging system to capture images in environments that are difficult to access due to the size of imaging detectors. Examples of such environments may include, for example, inside the human body, beyond a turn in a pipe or conduit, or inside a container or machine, such as a motor, that is currently operating. With respect to medical applications, for example, detector sizes may require large incisions for the detector itself to access the object of interest for imaging purposes.

BRIEF SUMMARY OF SOME EXAMPLES

According to some example embodiments, an imaging apparatus that is configured to operate at SWIR wavelengths is provided. The example imaging apparatus may include a flexible elongate member. The flexible elongate member may have a distal end and proximal end. The flexible elongate member may include, for example, a shortwave infrared (SWIR) imaging sensor, a distal lens optically coupled to the SWIR imaging sensor and disposed at the distal end of the flexible elongate member, the distal lens configured to focus light energy at the SWIR wavelength onto the SWIR imaging sensor, an illumination source configured to provide light energy at the SWIR wavelength at the distal end of the flexible elongate member for output to illuminate an object, and one or more control cables disposed within the flexible elongate member, the control cables enabling movement of the flexible elongate member. The imaging apparatus may also include a handle coupled to the flexible elongate member and mechanical controls operably coupled to the control cables for directing the flexible elongate member.

According to some example embodiments, another imaging apparatus is provided that may comprise a distal end, a proximal end, a shortwave infrared (SWIR) imaging sensor disposed at the distal end, a lens disposed on the distal end, the lens configured to focus light energy at the SWIR wavelength on the SWIR imaging sensor, SWIR anti-reflective coating disposed on the lens, and an illumination assembly configured to output illumination at the SWIR wavelength adjacent to the distal end toward an object, wherein the SWIR imaging sensor is configured to receive imaging light energy at the SWIR wavelength reflected from the object and focused through the lens.

An example method for imaging at the SWIR wavelengths is provided. The example method may comprise, for example, generating light energy at a shortwave infrared (SWIR) wavelength by an illumination source, projecting the light energy at a distal end of a flexible elongate member to illuminate an object with the light energy at the SWIR wavelength, receiving imaging light energy at the SWIR wavelength from the illuminated object at a distal lens of the flexible elongate member, focusing the imaging light energy at the SWIR wavelength onto a SWIR sensitive compact imager via the distal lens, and transmitting image data from the SWIR imaging sensor to a display.

BRIEF DESCRIPTION OF THE SEVERAL VIEWS OF THE DRAWING(S)

Having thus described some embodiments in general terms, reference will now be made to the accompanying drawings, which are not necessarily drawn to scale, and wherein:

FIG. 2 illustrates a distal end tip of a flexible elongate member of an example imaging apparatus according to various example embodiments;

FIG. 3A illustrates a cross-section front view of a fiber of the fiber optic bundle according to various example embodiments;

DETAILED DESCRIPTION

Figure 1:
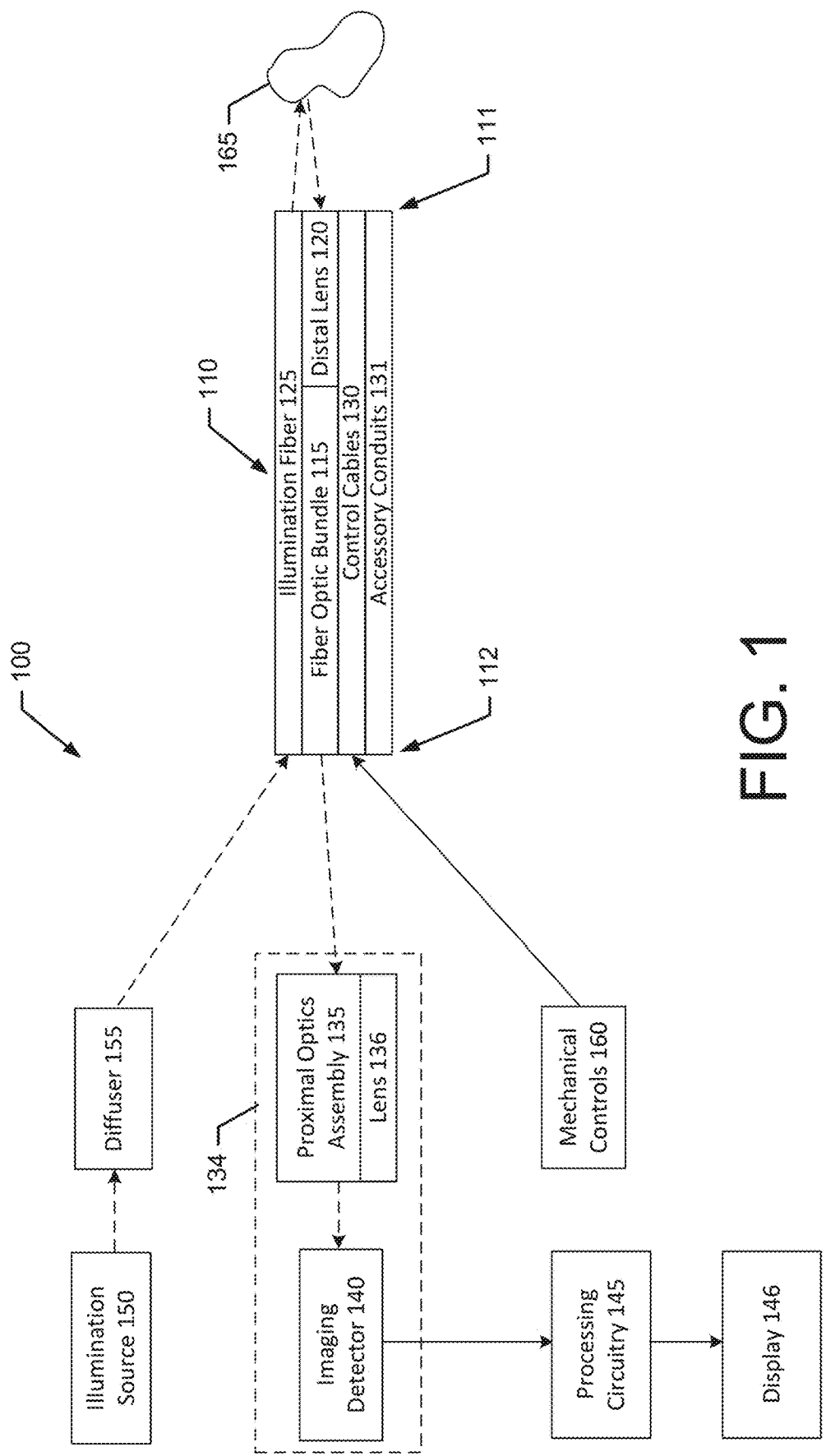
FIG. 1 illustrates a block diagram of an example imaging apparatus according to some example embodiments.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

As noted above, many current fiber optic bundles, which include coherent imaging fiber optic bundles, are specifically designed to operate in the visible spectrum. However, many imaging applications would benefit from imaging at other wavelengths that are not in the visible spectrum, such as short wave infrared (SWIR) wavelengths. For example, many materials being imaged, in particular biological tissues and fluids, may not support effective imaging in the visible spectrum due to issues with absorption and scatter in many environments. However, absorption and scattering may be greatly reduced in such applications if the imaging is performed at SWIR wavelengths. Unfortunately, many current fiber optic imaging bundles themselves may not be able to transmit nor support imaging at SWIR wavelengths due to issues such as crosstalk between the individual fiber cores of the bundle. Such crosstalk poses a technical problem that can inhibit the ability of the system to operate, for example, at the SWIR wavelengths, and therefore the benefits of imaging at SWIR wavelengths cannot be realized.

Accordingly, an example imaging apparatus is described herein that is capable of performing imaging at wavelengths in the shortwave infrared (SWIR) spectrum. The SWIR spectrum includes wavelengths from about 1.0 micrometer to about 1.7 micrometers. Various example embodiments of the invention may perform imaging at wavelengths, for example, of 1.5 micrometers, between greater than 1.0 micrometer to 1.7 micrometers, outside of the near infrared spectrum and visible light spectrum, or including the SWIR spectrum, the near infrared spectrum, and the visible light spectrum. The imaging apparatus may take a number of forms and may be implemented in a number of different applications. In some example embodiments, the apparatus may comprise an endoscope or a fiberscope. With respect to applications, the example imaging apparatus 100, as shown in FIG. 1, may be employing in medical imaging, mining, machine maintenance and repair, or the like. Because example embodiments operate in the SWIR spectrum (i.e., at SWIR wavelengths as defined herein), such apparatuses can realize significant advantages over, conventional systems, such as endoscopes and fiberscopes that operate in the visible spectrum (i.e., between 0.4 to 0.7 micrometers) or in the near infrared (NIR) spectrum (i.e., between 0.700 to 1.00 micrometers).

In this regard, the ability to image at the SWIR wavelengths offers a significant advantage with respect to reducing the scattering of light energy in the presence of lower density substances such as soft tissue. Imaging through, for example, biologic soft tissue can therefore be performed with high quality and with deeper imaging penetration due to the ability to operate at the SWIR wavelengths. As such, imaging at the SWIR wavelengths can offer increased imaging penetration into, for example, the body for medical imaging and diagnostic, which can offer a reducing in the physical impacts on the body. Additionally, the reduction in light scatter at the SWIR wavelengths can also reduce blurring and other effects of scattering thereby leading to improved image quality and higher diagnosis accuracy. These are just some examples of the benefits of SWIR wavelength operation in the context of medical imaging, while other benefits may also be realized in non-medical applications.

An example imaging apparatus, according to some example embodiments, may include a control assembly comprising an imaging detector configured to perform image capture at SWIR wavelengths. Additionally, the example apparatus may comprise a flexible elongate member that includes a fiber optic bundle that operably couples to the imaging detector to facilitate image capturing through the fiber optic bundle. According to some example embodiments, the fiber optic bundle may be configured for operation at the SWIR wavelengths to guide light energy reflected from an object of interest at SWIR wavelengths through the fiber optic bundle to the imaging detector for image capture. Functionally, the fiber optic bundle, due to its flexibility, length, and narrow cross-sectional diameter, may allow the imaging detector to capture images in locations where access may be limited (e.g., internal to a body or within a closed housing of a machine).

However, many conventional systems that employ fiber optic bundles have a drawback in the form of inter-core crosstalk. In this regard, because a fiber optic bundle includes a plurality of fibers. Each fiber may include a fiber core and cladding. The fibers, and thus the cores may be in close proximity to each other, and the evanescent fields that leak into the cladding of the fiber from the fiber core when guiding or propagating light energy can impact adjacent fiber cores leading to an issue called crosstalk that causes the transfer of light energy between a guiding fiber core to adjacent fiber cores. Additionally, because, in some instances, fiber cores may be fixed in adjacent parallel proximity across the entire length of the fiber optic bundle, an active fiber core (e.g., a fiber core that is guiding light of high intensity) may introduce significant crosstalk onto an adjacent fiber core because the cores remain in an adjacent physical relationship across an entire length of the fiber optic bundle. Additionally, while the degree of crosstalk may be dependent upon a number of factors, the wavelength of the light energy being guided by the fiber core may also effect the degree to which crosstalk occurs, and the guiding of SWIR wavelengths has been often found to commonly suffer from significant degrees of crosstalk between fiber cores. As a result, a technical problem exists relating to the ability to perform imaging at the SWIR wavelengths using fiber optic bundles.

According to some example embodiments, to reduce the impact of crosstalk in the fiber optic bundle, the fibers in at least an intermediate portion (or length) of the fiber optic bundle may be disposed in a non-parallel arrangement. In this regard, according to some example embodiments, two fibers of the fiber optic bundle need not be fixed in an adjacent, parallel alignment across the length of the fiber optic bundle. Rather, the fibers may be disposed in a non-aligned arrangement that promotes a non-parallel positional relationship between the fibers. As such, because the fibers are not adjacent across the length of the bundle, crosstalk between the corresponding cores of the fibers may be reduced. According to some example embodiments, the reduction in crosstalk realized in this manner can facilitate operation at the SWIR wavelengths.

According to some example embodiments, to introduce a non-parallel positional relationship between the fibers of the fiber optic bundle, the fiber optic bundle may be formed as a leached fiber bundle. According to some example embodiments, a leached fiber bundle may have an intermediate portion where the fibers are not aligned in parallel, but are permitted to move relative to each other. Such a structure may be formed via a leaching processes where a fiber optic bundle preform, that includes leachable spacers between the fibers, is, for example, subjected to an acid etch bath. After the spacers are leached away via the acid etch bath, the portions of the fibers that were subjected to the bath may be free to move relative to each other and be flexed or bent. However, to maintain coherency, the ends of the fiber optic bundle may remain fixed and the positioning of the fibers may be secured at the ends. As such, according to some example embodiments, this leached arrangement of the fibers can support a reduction in crosstalk and therefore facilitate operation of the example imaging apparatus at the SWIR wavelengths due to the non-parallel arrangement of fibers.

Having described some example embodiments in general terms, FIG. 1 provides a more detailed example embodiment of an imaging apparatus 100 in the form of a relational block diagram. The imaging apparatus 100 may be any type of imaging device including, but not limited to, an endoscope, fiberscope, or the like. In this regard, the imaging apparatus 100 or a portion thereof, may be a handheld device with, for example, a handle to permit a user to position and operate the device. The imaging apparatus 100 may include a control assembly 134 and a flexible elongate member 110, where the control assembly 134 is operably coupled to the flexible elongate member 110.

The control assembly 134 may include the imaging detector 140. The imaging detector 140 may be any type of device that is capable of capturing light energy, including light energy in the SWIR spectrum, and converting the received light energy into electrical signals for delivery to processing circuitry (e.g., processing circuitry 145) for image processing to develop a corresponding image. In this regard, the imaging detector 140 may be configured to receive imaging light energy at a SWIR wavelength that has been reflected from an object of interest 165 and guided to the imaging detector 140 via the fiber optic bundle 115. According to some example embodiments, the imaging detector 140 may be configured to perform imaging at a wide range of wavelengths, which may operate to permit imaging in both the visible spectrum and the SWIR. According to some example embodiments, the imaging detector 140 may include an image processor and may be configured to perform some or all image processing local to the imaging detector 140. The imaging detector 140 may comprise any type of digital camera, sensor array (e.g., charge coupled devices, active pixel sensors, etc.), or the like with sensitivity in the SWIR region of the electromagnetic spectrum. According to some example embodiments, an imaging detector 140 that comprises a digital camera may be specifically configured to operate to capture images at the SWIR wavelengths. The imaging detector 140 may be disposed at or towards a proximal end of the imaging apparatus 100 (i.e., opposite a distal end 111 of the flexible elongate member 110 as defined below) and may be operably coupled to the flexible elongate member 110, and more specifically the fiber optic bundle 115.

According to some example embodiments, the control assembly 134 may also include a proximal optics assembly 135 that is operably coupled to a proximal end of the fiber optic bundle 115. The proximal optics assembly 135 may include one or more lenses 136 configured to condition (e.g. focus) light energy received from the fiber optic bundle 115 for provision to the imaging detector 140. In this regard, according to some example embodiments, the proximal optics assembly 135 may include lenses shaped to magnify light energy in the SWIR spectrum from the fiber optic bundle 115 for projection onto the imaging detector 140.

According to some example embodiments, the imaging apparatus 100 may include or be operably coupled to processing circuitry 145. Processing circuitry 145 may be configured to receive electronic signals corresponding to an image capture of light energy and generate an image. The processing circuitry 145 may be configured to transmit the image to a display 146 (e.g., a liquid crystal display that may be stand-alone, a component of smartphone or tablet, or the like) for viewing by a user for the purpose of analyzing the image, for example, to make a diagnosis, or to navigate the flexible elongate member 110 into a desired position to capture an image of an object of interest 165. The processing circuitry 145 may include, for example, a processor and a memory, and the processor may be configured to execute instructions, code, or commands stored on the memory to cause the processing circuitry 145 to perform the functionalities of the processing circuitry 145 described herein. Alternatively, or additionally, the processor may be a hardware defined device configured to cause the processing circuitry 145 to perform the functionalities of the processing circuitry 145 describe herein, and may be embodied as, for example, a field programmable gate array (FPGA), an application specific integrated circuit (ASIC), or the like.

As mentioned above, the control assembly 134 may be operably coupled to the flexible elongate member 110. More particularly, the proximal optics assembly 135 and the imaging detector 140 of the control assembly 134 may be operably coupled to the fiber optic bundle 115 of the flexible elongate member 110. The flexible elongate member 110 may be configured to flex, bend, or otherwise articulate into various positions while supporting optical imaging functionalities. The orientation and positioning of the flexible elongate member 110 may be controllable by a user to position a distal end 111 of the flexible elongate member 110 in a desired position to perform an image capture of an object of interest 165. In this regard, the flexible elongate member 110 may have a distal end 111 which may, when in use, be closest to the object of interest 165 for image capture, and the flexible elongate member 110 may have a proximal end 112, which may be opposite the distal end 111 and operably coupled to the proximal optics assembly 135, or in some example embodiments physically coupled to a housing of the proximal optics assembly 135.

According to some example embodiments, the flexible elongate member 110 may include an illumination fiber 125, or a bundle of illumination fibers. The illumination fiber 125 may be an optical fiber that, in some example embodiments, is disposed within the flexible elongate member 110 and extends from the proximal end 112 of the flexible elongate member 110 to the distal end 111 of the flexible elongate member 110. The illumination fiber 125 may be configured to deliver or guide light energy from an illumination source 150 to the distal end 111 of the flexible elongate member 110 for output into the environment about the distal end 111 of the flexible elongate member 110 to illuminate an object of interest 165. According to some example embodiments, the illumination fiber 125 may be configured to guide light energy in the SWIR spectrum from the illumination source 150 to the distal end 111 of the flexible elongate member 110. According to some example embodiments, the illumination fiber 125 may be a multi-mode fiber.

While the illumination fiber 125 may be disposed within the flexible elongate member 110, the illumination fiber 125 may be a component of an illumination assembly. According to some example embodiments, the illumination assembly may include the illumination fiber 125 and an illumination source 150. According to some example embodiments, the illumination assembly may also include a diffuser 155, which according to some example embodiments, may be static or mechanically moveable or electroactively moveable.

The illumination source 150 may be any type of light generating device that can generate light energy at the SWIR wavelengths for provision to the illumination fiber 125. The illumination source 150 may, according to some example embodiments, be comprised of an incoherent source and filters configured to filter the incoherent light provided by the incoherent source to collectively operate as the illumination source 150. The illumination source 150 may be a laser, a light emitting diode (LED), or the like. According to some example embodiments, the illumination source 150 may be a super-luminescent diode (SLD). In some example embodiments, the illumination source 150 may be coupled directly to the illumination fiber 125. However, in some example embodiments, a diffuser 155 may be employed between the illumination source 150 and the illumination fiber 125. The diffuser 155 may be configured to diffuse or spread the light energy generated by the illumination source 150 across a surface in a relatively even fashion to minimize or remove high intensity areas or spots. By diffusing the light energy in this manner, the diffuser 155 may operate to reduce the spatial coherence of the light energy generated by the illumination source 150, thereby reducing speckle in images where the light energy used for illumination originates from the illumination source 150. According to some example embodiments, to further diffuse the light energy from the illumination source 150, or to diffuse effects on the light energy caused by propagation through the illumination fiber 125, a second diffuser may be placed at the distal end 111 of the flexible elongate member 110. Further, according to some example embodiments, the diffuser 155 may be a dynamic diffuser that changes (e.g., rotates) or adjusts to dynamically modify the diffusion of the light energy from the illumination source 150.

According to some example embodiments, to increase the illumination at desired wavelengths, for example at the SWIR wavelengths, the imaging environment may be treated with a photoreactive chemical such as a dye or particle. According to some example embodiments, the dye may be a fluorescent dye that is specifically developed to fluoresce at the SWIR wavelengths and offers enhanced emission of light energy at the SWIR wavelengths. An example of such a dye is indocyanine green (ICG), whereas an example of a particle is an engineered quantum dot. The added emission may cause increased intensity of light energy at the SWIR wavelengths to be received by the imaging detector 140 thereby improving contrast and image quality.

Additionally, according to some example embodiments, the illumination assembly may also include capabilities to illuminate at wavelengths other than SWIR wavelengths. In this regard, according to some example embodiments, the illumination assembly may include a separate illumination channel for, for example, visible light illumination. In this regard, the illumination assembly may include a visible light source that may be directed through another diffuser to an illumination fiber that guides visible illumination light energy to a distal end of the flexible elongate member 110 to illuminate the object of interest 165 with visible light. The visible light may be reflected from the object and be received at the imaging detector 140 via the fiber optic bundle 115 to perform imaging in the visible spectrum, in addition to being capable of permitting imaging in the SWIR spectrum.

The flexible elongate member 110 may, according to some example embodiments, include mechanical features that permit the flexible elongate member 110 to bend, flex, contort, or otherwise articulate into a variety of positions. In this regard, according to some example embodiments, the flexible elongate member 110 may include or be disposed within one or more flexible mechanical moldable coils (e.g., gooseneck flexible metal tubing) that permit a user to bend or otherwise articulate the flexible elongate member 110 into a desired position and the flexible elongate member 110 may maintain that desired position. Additionally or alternatively, the flexible elongate member 110 may be mechanically controllable via a control interface to reposition the flexible elongate member 110. In this regard, the imaging apparatus 100 may include mechanical controls 160 that may be operably coupled to control cables 130 (e.g., wires) that are disposed within the flexible elongate member 110. For example, the control cables 130 may be affixed to an inner surface of an external sheath of the flexible elongate member 110 and may be movable to reposition the flexible elongate member 110. In this regard, the mechanical controls 160 may include a user interface in the form of a joystick or other type of directional controls that may be physically connected to the control cables 130 such that, movement of the mechanical controls 160 causes movement of the control cables 130 in the flexible elongate member 110 to position (e.g., bend or otherwise articulate) the flexible elongate member 110. According to some example embodiments, the control cables 130 may be affixed in a manner such that the directional controls operate to maneuver a portion near the distal end 111 (e.g., a tip) of the flexible elongate member 110. According to some example embodiments, the directional controls may electrically connected to electromechanical actuators (e.g., servos or the like) that receive electrical signals from the directional controls and cause the electromechanical actuators to move thereby causing the control cables 130 that are connected to the electromechanical actuators to move and position the flexible elongate member 110.

Additionally, according to some example embodiments, the flexible elongate member 110 may also include one or more accessory conduits 131. In regard, according to some example embodiments, an accessory conduit 131 may be an open tube in the flexible elongate member 110 that would permit a user to guide an item from the proximal end 112 of the flexible elongate member 110 to the distal end 111 of the flexible elongate member 110. For example, an accessory conduit 131 may be configured to permit a tool (i.e., a pincer, cutting tool, cauterizing tool, or the like) to be inserted into a proximal end of the accessory conduit 131 and pushed through the accessory conduit 131 to extend out of the distal end 111 of the accessory conduit 131 and the distal end 111 of the flexible elongate member 110. In this manner, a user may be capable of performing actions at the distal end 111 of the flexible elongate member 110 while visualizing the environment at the distal end 111 of the flexible elongate member 110 via the operation of the imaging detector 140 as further described herein. Additionally or alternatively, an accessory conduit 131 may be configured to guide fluids (e.g., water) or gases (e.g., air) into a space at the distal end 111 of the flexible elongate member 110 as required for certain applications of the imaging apparatus 100.

As indicated above, the flexible elongate member 110 may also include a fiber optic bundle 115. According to some example embodiments, the fiber optic bundle 115 of the flexible elongate member 110 may be operably coupled between the proximal optics assembly 135 and a distal lens 120 of the flexible elongate member 110. The distal lens 120 may be disposed at the distal end 111 of the flexible elongate member 110 and may be optically coupled to the fiber optic bundle 115. According to some example embodiments, the distal lens 120 may comprise a plurality of optic devices (e.g., lenses). According to some example embodiments, the distal lens 120 may be a gradient index lens (i.e., GRIN lens) and may be configured to focus light energy received at the distal end 111 of the flexible elongate member 110 onto the distal end of the fiber optic bundle 115 to be guided via the fiber optic bundle 115 to the imaging detector 140. The distal lens 120 may be specifically designed for imaging of wavelengths throughout the SWIR wavelength. According to some example embodiments, the distal lens 120 may be designed for telecentricity in the image space, which may support coupling to the imaging fiber bundle 115. Also, the distal lens 120 may be embodied as a compact, small diameter lens (e.g. diameter of about 2 millimeters) thereby supporting a relatively small form factor and the capability to investigate narrowly constricted locations of interest for imaging. The distal lens 120 may be configured to focus light energy in the SWIR spectrum. The distal lens 120 may be relatively small in size for application at the distal end 111 of the flexible elongate member 110 but still support high resolution imaging, particularly in the SWIR spectrum.

With respect the distal end 111 of the flexible elongate member 110, FIG. 2 illustrates a view of an example tip end 200. In this regard, the tip end 200 may include a casing 210 and a plurality of openings that serve various purposes. The tip end 200 may include an illumination opening 215 that is aligned with the illumination fiber 125 to output illumination light energy from the illumination fiber 125. The tip may also include openings 230, 240, and 250, which may be accessory openings that align with a corresponding accessory conduit 131. Additionally, the tip end 200 may include an optical opening 220. The optical opening 220 may be aligned with the fiber optic bundle 115 and the distal lens 120 and configured to receive light energy reflected off of an object for delivery to the imaging detector 140 via the distal lens 120 and the fiber optic bundle 115.

As mentioned above, the fiber optic bundle 115 may be specifically configured to guide light energy in the SWIR spectrum to support imaging at SWIR wavelengths. Additionally, the fiber optic bundle 115 may be configured to support transmission of light energy at a SWIR wavelength, including, according to some example embodiments, multimode, near single mode, or single mode transmission. According to some example embodiments, the fiber optic bundle 115 may be structurally designed to include a plurality of individual fibers (e.g., 321 of FIG. 3A) that make up the conglomerate fiber optic bundle 115. Referring to FIG. 3A, each fiber 321 may comprise, for example, a core 322 and cladding 323. The core 322 may be formed as a thread of glass or other energy conductor that is configured to propagate light energy in an efficient manner. The cladding 323 may be disposed about and outer surface of the core 322 in the form of a sheath. The cladding 323 may also be formed of glass, but may provide an index of refraction that differs from the index of refraction of the core 322.

To contribute to the ability to support operation at a SWIR wavelength, according to some example embodiments, a the fiber optic bundle 115 may have a defined relationship between the index of refraction of the core 322 and the index of refraction of the cladding 323. In this regard, for example, a percent decrease of the index of refraction of the cladding 323 to the index of refraction of the fiber optic core 322 may be defined. For example, the percent decrease of the index of refraction of the cladding 323 to the index of refraction of the fiber optic core 322 may be between about 5% and 2% or in some cases 3.1%. Additionally, a relationship may be defined between the percent area of the fiber optic core 322 to the fiber optic cladding 323 for a fiber 321. Each of the plurality of fiber 321 may define a cross-sectional area. For example, the percent area of the fiber optic core 322 to the fiber optic cladding 323 may be about 40% for the core 322 and 60% for the cladding 323. As such, according to some example embodiments, to contribute to the ability to support operation at the SWIR wavelengths, the cladding 323 may have a greater portion of the cross-sectional area than the core 322. According to some example embodiments, the cladding 323 may be about 55% to 65% of the cross-sectional area of the fiber 321.

Figure 3B:
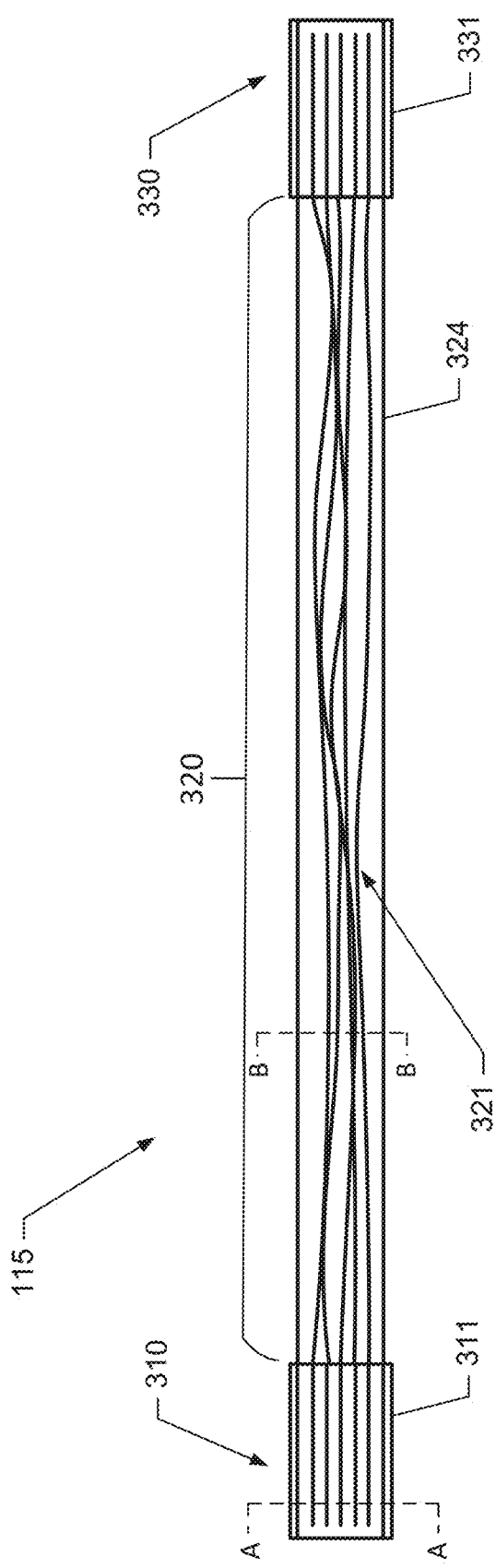
FIG. 3B illustrates a cross-section side view of an fiber optic bundle according to various example embodiments.

The fiber optic bundle 115 may be formed in a number of different structures to support operation at the SWIR wavelengths. According to some example embodiments, the fiber optic bundle 115 may be a coherent imaging fiber bundle where individual fibers 321 of the fiber optic bundle 115 are aligned at the ends of the fiber optic bundle 115. In this regard, FIG. 3B illustrates one example of a fiber optic bundle 115 that can support operation at the SWIR wavelengths. The fiber optic bundle 115 may comprise a proximal end 310, an intermediate portion 320, and a distal end 330. A length of the fiber optic bundle 115 may depend on the application for the imaging apparatus 100, but, according to some example embodiments, the length of the fiber optic bundle 115 may be 1 meter. The fiber optic bundle 115 may include a plurality of fibers 321, with each individual fiber 321 including a core 322 and cladding 323. The composite diameter of an individual fiber 321 (i.e., the diameter from and to an outer surface of the cladding 323) may have a cross-sectional diameter of, for example, 8 micrometers.

According to some example embodiments, the fiber optic bundle 115 may provide a wider field of view than a single mode fiber due to, at least in part, the plurality of fibers 321 in the fiber optic bundle 115. In this regard, the plurality of fibers 321 may operate to increase the image area relative to a single fiber. In some instances, a single fiber approach may require a scanning mechanism for building up an image, whereas, according to some example embodiments, the fiber optic bundle 115, with the plurality of fibers 321, may capture an image in a wider field of view without the use of such as scanning mechanism or other supporting components or processes that may be used to support effective single mode operation with a single fiber.

Figure 4B:
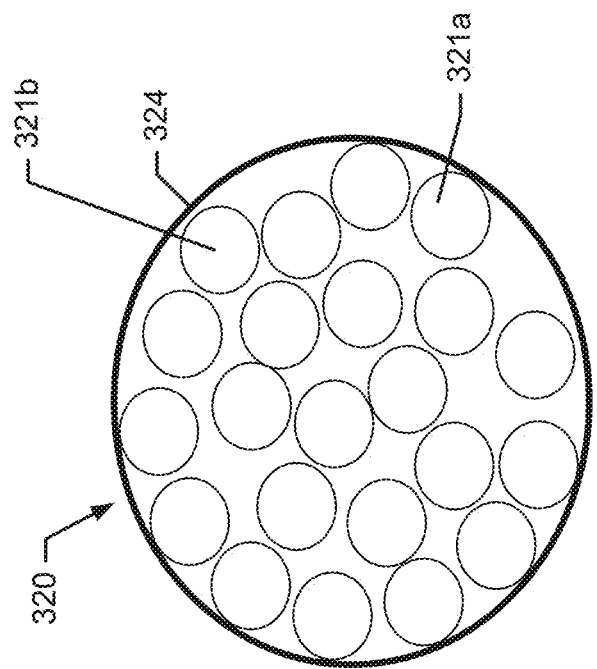
FIG. 4B illustrates a cross-section view of an intermediate portion of the fiber optic bundle of FIG. 3B taken at B-B according to various example embodiments.
Figure 4A:
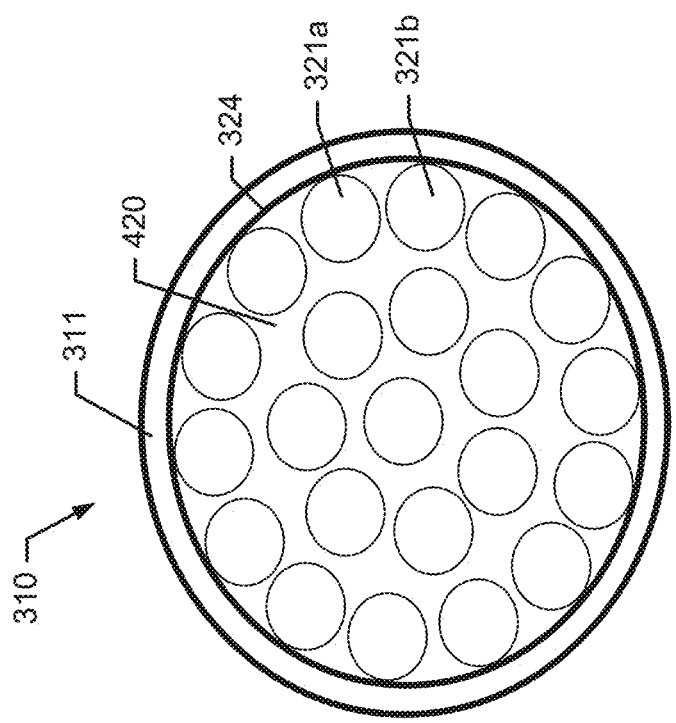
FIG. 4A illustrates a cross-section view a proximal end of the fiber optic bundle of FIG. 3B taken at A-A according to various example embodiments.

At the proximal end 310 (and similarly the distal end 330), the plurality of fibers 321 may be arranged in an organized fashion as shown in the cross-sectional view of FIG. 4A, taken at A-A. According to some example embodiments, the plurality of fibers 321 may be organized in a hexagonal arrangement or pattern. In this regard, the proximal end 310 of the fiber optic bundle 115 may have a length (e.g., end length) where ferrule 311 may hold the plurality of fibers 321 in an aligned, parallel arrangement. According to some example embodiments, the bundle cladding 420 may also assist with holding the plurality of fibers 321 in place and may be comprised of, for example, air (e.g., through the use of cladding spacers). According to some example embodiments, the bundle cladding 420 may also be comprised of glass that, for example, may be configured differently from the fibers 321. To hold the plurality of fibers in the fixed position, a ferrule 311 may be crimped or otherwise applied to the proximal end 310. Although FIG. 4A illustrates a cross-sectional view of the proximal end 310, the distal end 330 may be identical with the exception of being disposed at an opposite end of the fiber optic bundle 115 and held together by a ferrule 331. In example embodiments where the fiber optic bundle 115 is a coherent bundle, individual fibers 321a and 321b may be positioned in corresponding locations on the proximal end 310 and the distal end 330. Further, as illustrated in FIG. 4A, fiber 321a may be positioned adjacent to fiber 321b at the proximal end 310 and the distal end 330 of the fiber optic bundle 115.

With respect to the intermediate portion 320, the plurality of fibers 321 may be held within a flexible sheath 324, which may extend into the proximal end 310 and the distal end 330. Within the intermediate portion 320, the plurality of fibers 321 may be non-parallel and have a non-aligned arrangement. As shown in FIG. 3B, the parallel, aligned arrangement of the plurality of fibers 321 in the proximal end 310 and the distal end 330 does not continue into the intermediate portion 320. In the intermediate portion 320, according to some example embodiments, adjacency relationships between the fibers 321 may be non-uniform, which may contribute to a reduction in crosstalk between the fibers 321 and their respective cores 322. The fibers 321 in the intermediate portion 320 may, according to some example embodiments, be free to move relative to each other and be reorganized into different relative orientations due to, for example, movement, bending, or otherwise articulation of the fiber optic bundle 115.

In this regard, for example, fibers 321a and 321b are shown as being adjacent to each other at the proximal end 310 and the distal end 330, as shown in FIG. 4A. However, in the cross-sectional view of the FIG. 4B taken at B-B of the fiber optic bundle 115 as shown in FIG. 3B, the fiber 321a is not adjacent to the fiber 321b. Because the fibers 321 are permitted to move relative to each other in the intermediate portion 320, rearrangement of the fibers 321 can occur, for example during bending, flexing, or other type of articulation of the fiber optic bundle 115. As such, the fibers 321a and 321b do not remain adjacent to each other across the length of the fiber optic bundle 115 and therefore the impact of crosstalk specifically between the two fibers is reduced, thereby promoting efficient propagation of light energy at the SWIR wavelengths.

As mentioned above, one technique for forming and arrangement of non-parallel or non-aligned fibers 321 in the intermediate portion 320 may be via a leaching process. Examples of a fiber optic bundles 115 that are leached, according to some example embodiments, include Schott North America, Inc.'s line of leached fiber optic bundles. To form a leached fiber bundle, the fibers 321 may be stacked, for example, in a hexagonal arrangement or pattern. A preform of the fiber optic bundle 115 may be constructed that includes leachable spacers between the fibers 321. The preform of the fiber optic bundle 115 may then be drawn to a desired length and desired fiber and fiber core diameters. According to some example embodiments, the length of the fiber optic bundle 115 may be 1 meter and the diameter of the fibers 321 may be 8 micrometers. The proximal and distal ends of the fiber optic bundle 115 may be capped with a ferrule such that the proximal and distal ends remain coherent as described above. The leachable spacers may be soluble in an etching acid. As such, when the intermediate portion 320 is dipped or otherwise subjected to the etching acid bath, the spacers may be leached away and the fiber cores 321 in the intermediate portion 320 may be free to move relative to each other and be bent or flexed.

While the leaching process described above may be one technique for reducing crosstalk to support operation of the imaging apparatus 100 at the SWIR wavelengths, other fiber optic bundle structures and techniques may also be employed. In this regard, an anti-crosstalk coating (e.g., an energy absorbent coating) may be applied to each fiber core. In this manner, crosstalk may be limited due to a reduction in the amplitude of the evanescent field generated by each fiber core.

As mentioned above, propagation of SWIR wavelengths in the fiber optic bundle 115 may also be supported, according to some example embodiments, due to characteristics of the individual fibers 321 of the bundle. Supported propagation modes within a fiber 321 may be governed by a dimensionless quantity known as the V-number, which is defined as $$V = \frac{2\pi}{\lambda} aNA,$$

where $\lambda$ is the wavelength of light and a is the fiber optic core radius. NA represents the numerical aperture of the fiber 321, which dictates the largest acceptance angle that the fiber 321 will permit for propagation of the light in the fiber optic core 322 of a step index fiber (i.e., a fiber where the index of refraction is different between the core and the cladding). The numerical aperture (dimensionless) is value that characterizes the range of angles over which light can be accepted or emitted and is defined as $NA = \sqrt{n_{core}^2 - n_{cladding}^2}$, where $n_{core}^2$, is the index of refraction of the core and $n_{cladding}^2$, is the index of refraction of the cladding. Propagation mode confinement by an individual fiber 321 of the fiber optic bundle 115 may be a factor that contributes to maintaining proper imaging in the fiber optic bundle 115. In this regard, if a propagation mode is not confined to the individual fiber, crosstalk from fiber to fiber may operate to scramble the image. As is seen by the V-number, several parameters dictate the supported propagation modes of the fiber 321. Specifically for SWIR wavelengths, according to some example embodiments, the radius of the fiber optic core 322 can dictate the ability of the fiber 321 to support certain propagation modes. According to some example embodiments, a fiber optic core radius that may support propagation modes for the SWIR wavelengths may have the area of the fiber optic core 322 that is 40% of the total cross-sectional area of the fiber 321, while the area of the cladding 323 (e.g., alone or with other surrounding materials) may be 60% of the cross-sectional area of the fiber 321. In some instances, this is in contrast to other fiber optic bundles that do not support propagation modes for the SWIR wavelengths, whereby the fiber optic core to fiber optic cladding area percentages may be 50% and 50%, respectively.

Further, to support propagation modes for the SWIR wavelengths, the fiber 321 may have a high NA value for optical fibers (e.g., an NA value greater than 0.25, such as 0.4), which is correlated with having relatively stronger propagation mode confinement in general. Additionally, a higher NA value may also have the ability to achieve stronger confinement across a broader wavelength range than low NA fibers. The manipulation of the NA of the fiber 321 may be dependent upon the materials used for both the fiber optic core 322 and fiber optic cladding 324. According to some example embodiments, a fiber 321 with an index percent decrease between the fiber optic core and the fiber optic cladding of 3.1%, which may result in an NA=0.4. This is in contrast to, for example, a standard telecommunications single mode fiber, which does not support propagation modes for the SWIR wavelengths and has a fiber optic core to fiber optic index percent decrease between the fiber optic core and the fiber optic cladding of 0.36%, resulting in an NA=0.19. The core radius and the NA may operate to increase the ability of an individual fiber 321 to maintain light energy within that fiber's core 322 over a larger range of wavelengths, including the SWIR. The core radius and the NA may also serve to confine the light in an individual fiber optic core 322 over longer propagation distances, which may also limit the amount of light that escapes or leaks from the core to the cladding 323 and on to a neighboring fiber 321 in the bundle 115. Such a reduced degree of light leakage from the individual fiber optic core 322 into the cladding 323 may operate to reduce, for example, crosstalk particularly at longer wavelengths, such as those in the SWIR, where crosstalk is more prevalent.

Additionally, propagation of longer wavelengths, such as SWIR wavelengths, may also be supported, according to some example embodiments, by an index step size between the fiber optic cores 322 and the cladding 323 being relatively large as compared to, for example, other fiber bundles. In this regard, the index of refraction of the fiber optic cores 322 may be different from the index of refraction of the cladding 323 by an amount that may be referred to as the index step size. A larger index step size between the core 322 and the cladding 323 of the fiber optic bundle 115 may operate to increase an ability to maintain light energy within the fiber optic cores 322 and limit the amount of light that escapes or leaks from the fiber optic cores 322. Such a reduced degree of light leakage from the fiber optic cores 322 into the cladding 323 may operate to reduce, for example, crosstalk. For larger wavelengths, such as the SWIR wavelengths, the index step size between the fiber optic cores 322 and the cladding 323 can be configured to support the desired wavelength.

Additionally, leached fiber bundles may be able to propagate the SWIR wavelengths because the index step size between the core 322 and the cladding 323 may be rather large compared to other fiber bundles. When a larger the step size between core and cladding index of refraction is present, the fiber 321 may be better suited to contain the light within the core 322 because less light may leak into the cladding 323 which reduces crosstalk. This may be especially true for larger wavelengths (e.g., SWIR wavelengths) as the step index size difference between the core 322 and the cladding 323 may need to be greater to support the propagation mode of interest. According to some example embodiments, an air clad fiber bundle may operate in this manner because the step in index from the core glass to air is very large.

Finally, the spacing between the fiber cores, i.e. the cladding thickness, plays a large role in the interaction between cores. The larger the thickness the less likely interaction between cores can occur; however, this comes at a cost of degraded resolution due to an associated reduction in core packing. Additionally, according to some example embodiments, dopants of the fiber optic cores 321 may also operate to support the operation of the fiber optic bundle 115 at the SWIR wavelengths. For example, according to some example embodiments, the fiber optic cores 321 may be doped with Germanium (GE) and the cladding 323, in the form of glass, may be doped with Fluorine (F) to increase the index step size. Depending on dopant amounts, absorption in the SWIR may be high, which would degrade the fiber optic cores' ability to effectively transfer the light energy and thus an image.

According to some example embodiments, the diameters of the fiber optic cores 321 may be non-uniform. In this regard, some fiber optic cores 321 may have larger or smaller diameters than other fiber optic cores 321. Differing diameters amongst the fiber optic cores 321 may also operate to reduce the amount of light energy leakage from a fiber optic core 321 to another fiber optic core 321, when the fiber optic bundle 115 is considered in the aggregate. Since the different diameters may cause the respective fiber optic cores 321 to exhibit different supported propagation mode parameters, crosstalk may again be limited by the introduction of fiber optic cores 321 of differing diameters.

Additionally, the spacing between the fiber optic cores 321 may also be considered to improve performance of the fiber optic bundle 115 at the SWIR wavelengths. In this regard, the spacing between the fiber optic cores 321 or the thickness of the cladding 323 may have an effect, and in in some instances a large effect, on the interaction between the fiber optic cores 321 with respect to, for example, crosstalk between the fiber optic cores 321. In general, cladding 323 having a larger thickness and thus increased spacing between the fiber optic cores 321 may permit less interaction between the fiber optic cores 321 and thus less crosstalk. However, according to some example embodiments, such increased spacing between the fiber optic cores 321 may cause degraded resolution due to an associated reduction in core packing (i.e., closeness between the cores).

Additionally, according to some example embodiments, certain glass types may have the advantage of support propagation modes over smaller bend radii than those of other glass types. In this regard, fiber optic bundles 115 composed of soft glasses (e.g., glasses formed of two types of lead silicate) may have the ability to support the SWIR wavelength propagation at a bend radius of 9 millimeters. This is compared to glasses of a more rigid variety, such as silica, that can only support a bend radius of 60 millimeters. Bend loss associated with the differing glasses can be attributed to the NA of the fiber 321, with again higher NA fibers 321 suffering less bend loss than lower NA fibers. Accordingly, crosstalk may be reduced at smaller bend radii, which again can be beneficial to the transmission of the SWIR wavelengths. Soft glasses may have higher NAs and are therefore less susceptible to bend loss compared to the more rigid glasses.

The components described herein, have been described with respect to supporting operation of an imaging apparatus at the SWIR wavelengths. Additionally, according to some example embodiments, the components described herein may also support operation at wavelengths other than SWIR wavelengths. For example, according to some example embodiments, an imaging apparatus may support imaging at NIR wavelengths as well as SWIR wavelengths. As such, according to some example embodiments, an imaging apparatus may be configured to perform imaging operations at different wavelengths to generate multi-band imaging (e.g., SWIR and NIR imaging).

Figure 5:
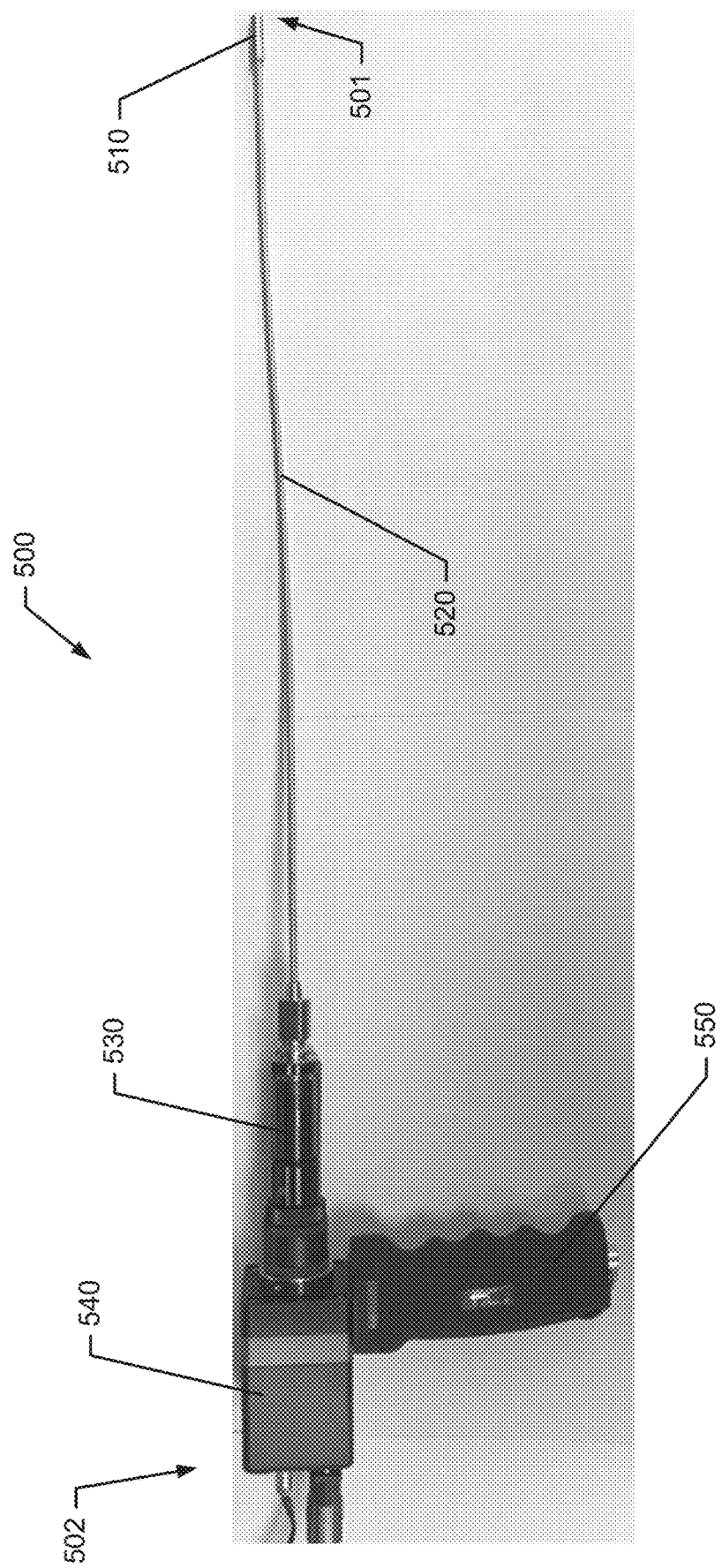
FIG. 5 illustrates an example endoscope according to some example embodiments.

Having described example embodiments of the imaging apparatus 100 in a more general sense, FIG. 5 illustrates an example imaging apparatus in the form of a handheld portion of an endoscope 500, according to some example embodiments. In this regard, the endoscope 500 may have a distal end 501 and a proximal end 502. Further, the endoscope 500 may comprise distal tip 510, a flexible elongate member 520, a proximal optics assembly 530, an imaging detector 540, and a handle 550. In this regard, the distal tip 510 may house a distal lens (e.g., distal lens 120) and be affixed to a distal end of the flexible elongate member 520. The flexible elongate member 520 may include a fiber optic bundle (e.g., fiber optic bundle 115) and an illumination fiber (e.g., illumination fiber 125). The proximal optics assembly 530 may be affixed to a proximal end of the flexible elongate member 520 and may be structured and configured to operate in the same manner as the proximal optics assembly 135. Further, the imaging detector 540 may be structured and configured to operate in the same manner as the imaging detector 140. Finally, the handle 550 may be included to facilitate user manipulation of the endoscope 500 and the flexible elongate member 520 of the endoscope 500.

Figure 9:
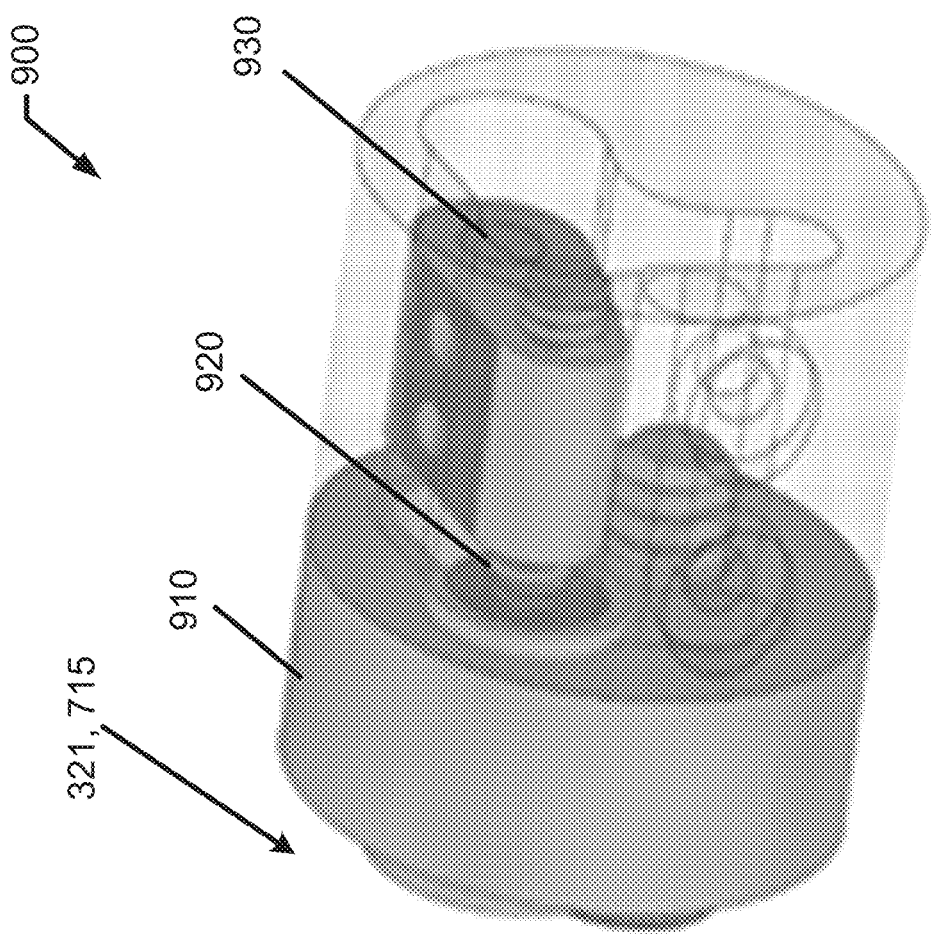
FIG. 9 illustrates an example device to provide a focusing capability.

In some embodiments, a focusing capability may be built into distal tip 510 at distal end 501 of endoscope 500. For example, FIG. 9 includes example focusing device 900. Focusing device 900 may include micro stepper motor 910, lead screw 920, and lens holder 930. Micro stepper motor 910 may drive distal lens 120 or distal lens 720 back and forth to provide focus (or imaging) to various objects at different distances from the distal end 111. In some embodiments, the focusing device 900, including the micro stepper motor 910, has a maximum diameter of 3.4 mm. Lead screw 920 is attached to the shaft of micro stepper motor 910 and may spin clockwise or counterclockwise. In some embodiments, lens holder 930 holds distal lens 120 or distal lens 720 and/or is coupled to distal lens 120 or distal lens 720. Lens holder 930 may be coupled to micro stepper motor 910 via lead screw 920. As lead screw 920 spins, lens holder 930 may ride up and down lead screw 920 and changes the focus of the image data collected allowing for more accurate imaging.

In one embodiment, the plurality of fiber 321 may be rigidly coupled to the housing of micro stepper motor 910 such that the coherent bundle (e.g., fiber 321) stays fixed in place behind the moving lens. Light (e.g., SWIR wavelengths) may be focused using distal lens 120 and propagate through the fiber bundles as described above.

In another embodiment, the housing of micro stepper motor 910 may be coupled to or include the SWIR imaging sensor 715. Distal lens 720 may focus the light to SWIR imaging sensor 715, while micro stepper motor 910 may allow adjustment of the focus to enable accurate data collection.

Figure 10:
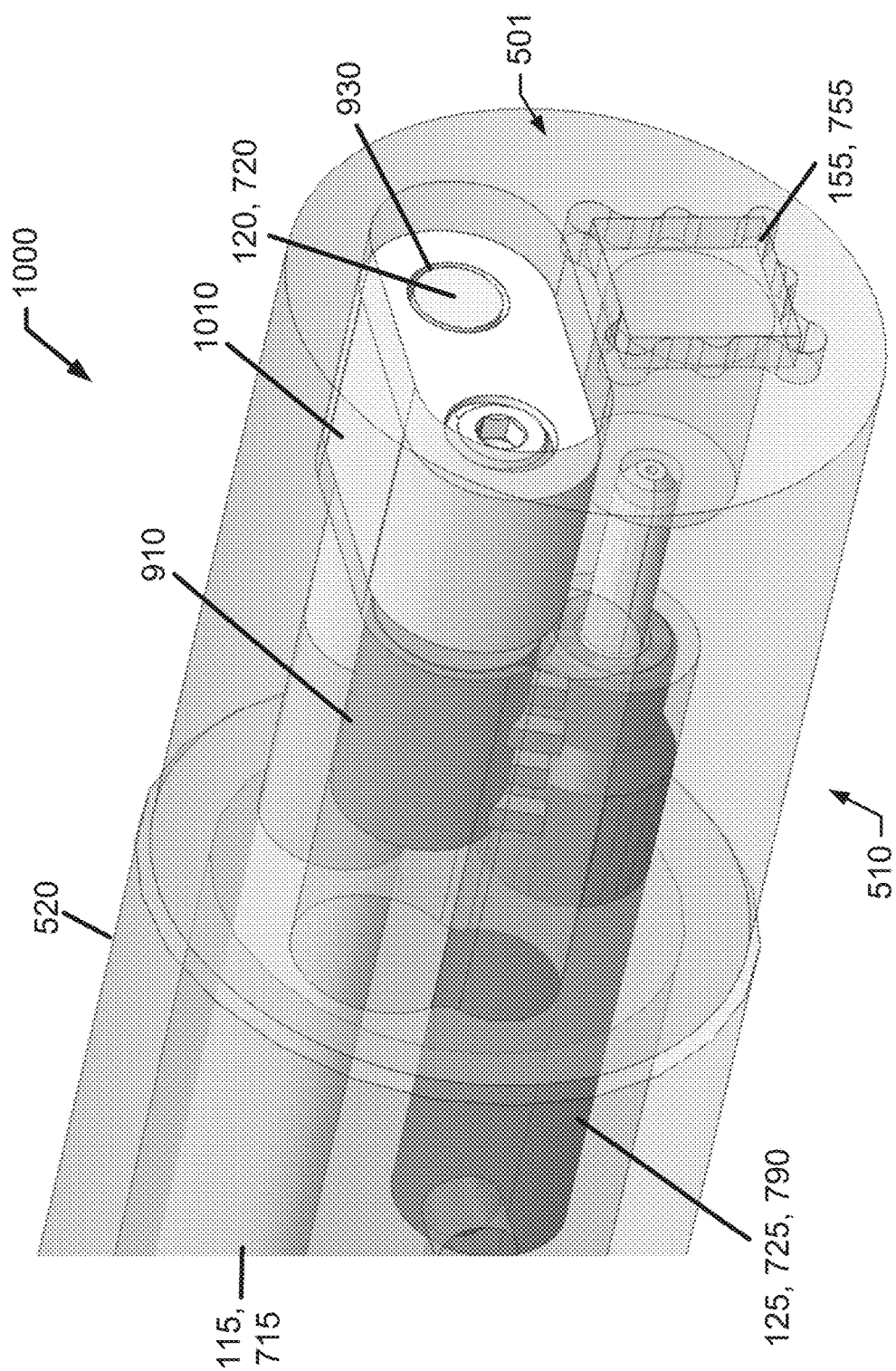
FIG. 10 illustrates an example distal tip of an endoscope.

FIG. 10 illustrates an example of a distal tip of endoscope 1000. Distal tip of endoscope 1000 may include endoscope 500, flexible elongate member 520, distal tip 510, and distal end 501. FIG. 10 shows an example embodiment illustrating various components from FIGS. 1, 5, 7, and 9. In one embodiment, distal tip of endoscope 1000 includes diffuser 155 or 755 that diffuses light in, for example, the SWIR spectrum, from illumination fiber 125 or 725 or from compact SWIR illumination source 790. Distal tip of endoscope 1000 may also include stepper motor 910 that spins lead screw 920 (not shown in FIG. 10) on which nut 1010 slides up and down changing the focus for distal lens 120 or distal lens 720 held in place by lens holder 930. FIG. 10 also depicts placement of the fiber optic bundle 115 or SWIR imaging sensor 715 that are optically coupled to distal lens 120 or distal lens 720 and receives, for example, light in the SWIR spectrum propagated through diffuser 155 or 755 and reflected off an object of interest 165.

Figure 6:
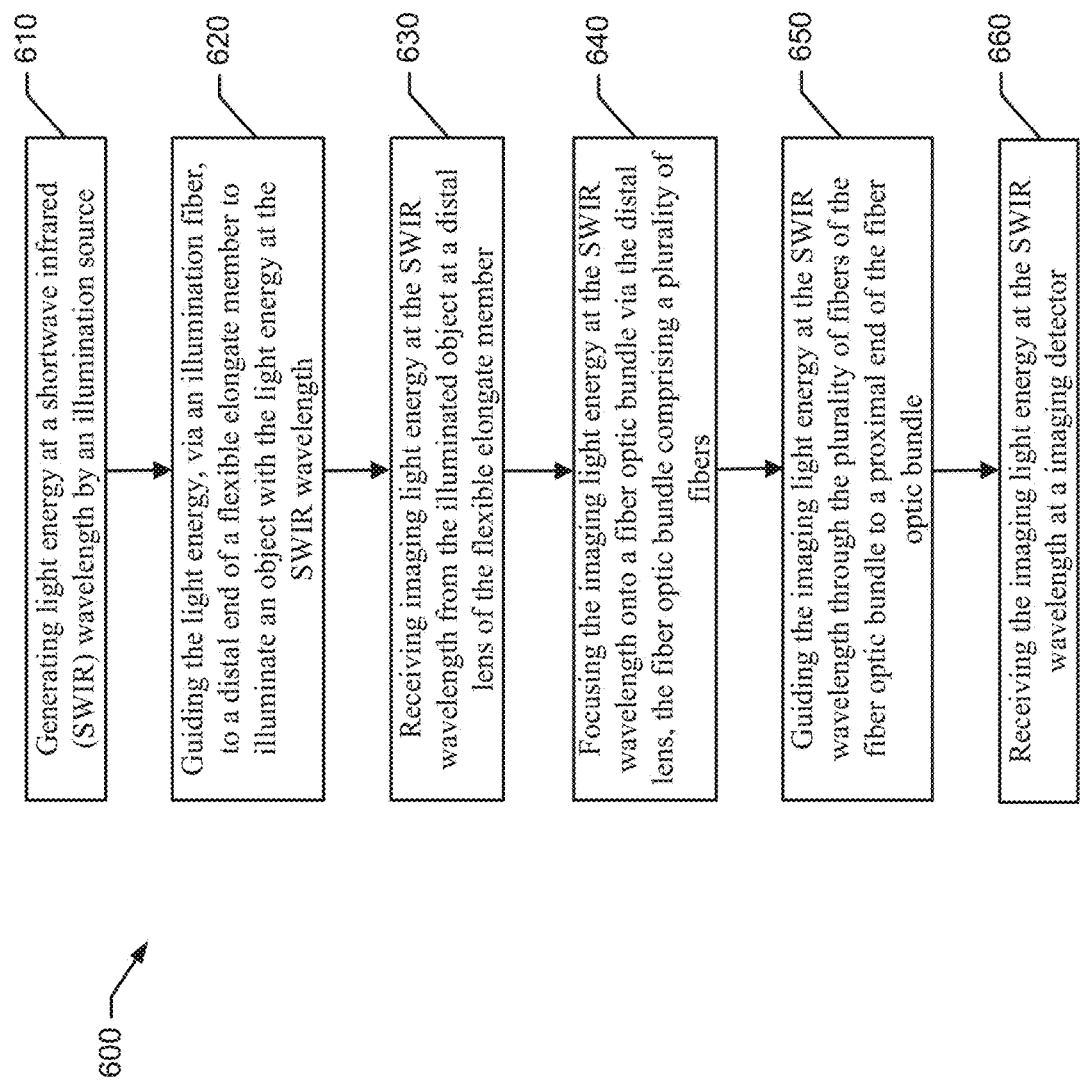
FIG. 6 illustrates a block diagram of an example method for imaging according to various example embodiments.

FIG. 6 illustrates a block diagram of an example method 600 for imaging according to various example embodiments. In accordance with the description above, according to some example embodiments, the example method 600 may comprise, at 610, generating light energy at a shortwave infrared (SWIR) wavelength by an illumination source, and, at 620, guiding the light energy, via an illumination fiber, to a distal end of a flexible elongate member to illuminate an object with the light energy at the SWIR wavelength. Additionally, at 630, the example method 600 may comprise receiving imaging light energy at the SWIR wavelength from the illuminated object at a distal lens of the flexible elongate member. In this regard, the imaging light energy may be light energy at the SWIR wavelength guided by the illumination fiber and reflected off of the object. Further, at 640, the example method 600 may comprise focusing the imaging light energy at the SWIR wavelength onto a fiber optic bundle via the distal lens. In this regard, the fiber optic bundle may comprise a plurality of fibers. Additionally, the example method may comprise, at 650, guiding the imaging light energy at the SWIR wavelength through the plurality of fibers of the fiber optic bundle to a proximal end of the fiber optic bundle, and, at 660, receiving the imaging light energy at the SWIR wavelength at an imaging detector.

Additionally, according to some example embodiments, the fiber optic bundle of the example method 600 may comprise a portion (e.g., an intermediate portion) where the plurality of cores are disposed in a non-parallel arrangement, for example, due to a leaching process. Additionally or alternatively, the fiber optic bundle of the example method 600 may comprise a first fiber core and a second fiber core and the first fiber core may be disposed adjacent to the second fiber core at the distal end and the proximal end of the fiber optic bundle. However, the first fiber core need not be adjacent to the second fiber core at an intermediate portion of the fiber optic bundle.

Additionally or alternatively, the example method 600 may comprise passing the light energy generated by the illumination source through a diffuser prior to guiding the light energy to the distal end of the flexible elongate member to reduce spatial coherence of the light energy generated by the illumination source. Additionally or alternatively, according to some example embodiments, the example method may also comprise guiding the imaging light energy at the SWIR wavelength through the fiber optic bundle at the SWIR wavelength as a multi-mode, near single mode, or single mode transmission. Additionally or alternatively, each fiber of plurality of fibers of the fiber optic bundle may comprise a core and cladding and each fiber defines a cross-sectional area. According to some example embodiments, about 55% to 65% of the cross-sectional area of a fiber of the fiber optic bundle may be attributed to the cladding. Additionally or alternatively, an index of refraction for the cladding may be about 5% to 2% lower than the index of refraction of the core. Additionally or alternatively, the example method 600 may comprise, according to some example embodiments, causing the flexible elongate member to bend or otherwise articulate in response to actuation of a mechanical control to move a control cable in the flexible elongate member. According to some example embodiments, the example method 600 may also comprise, according to some example embodiments, performing image processing on signals corresponding to the imaging light energy at the SWIR wavelength received at the imaging detector to generate an image of the object. Additionally or alternatively, the example method 600 may include adding a fluorescent dye to the object that reflects light energy at the SWIR wavelength.

Figure 7:
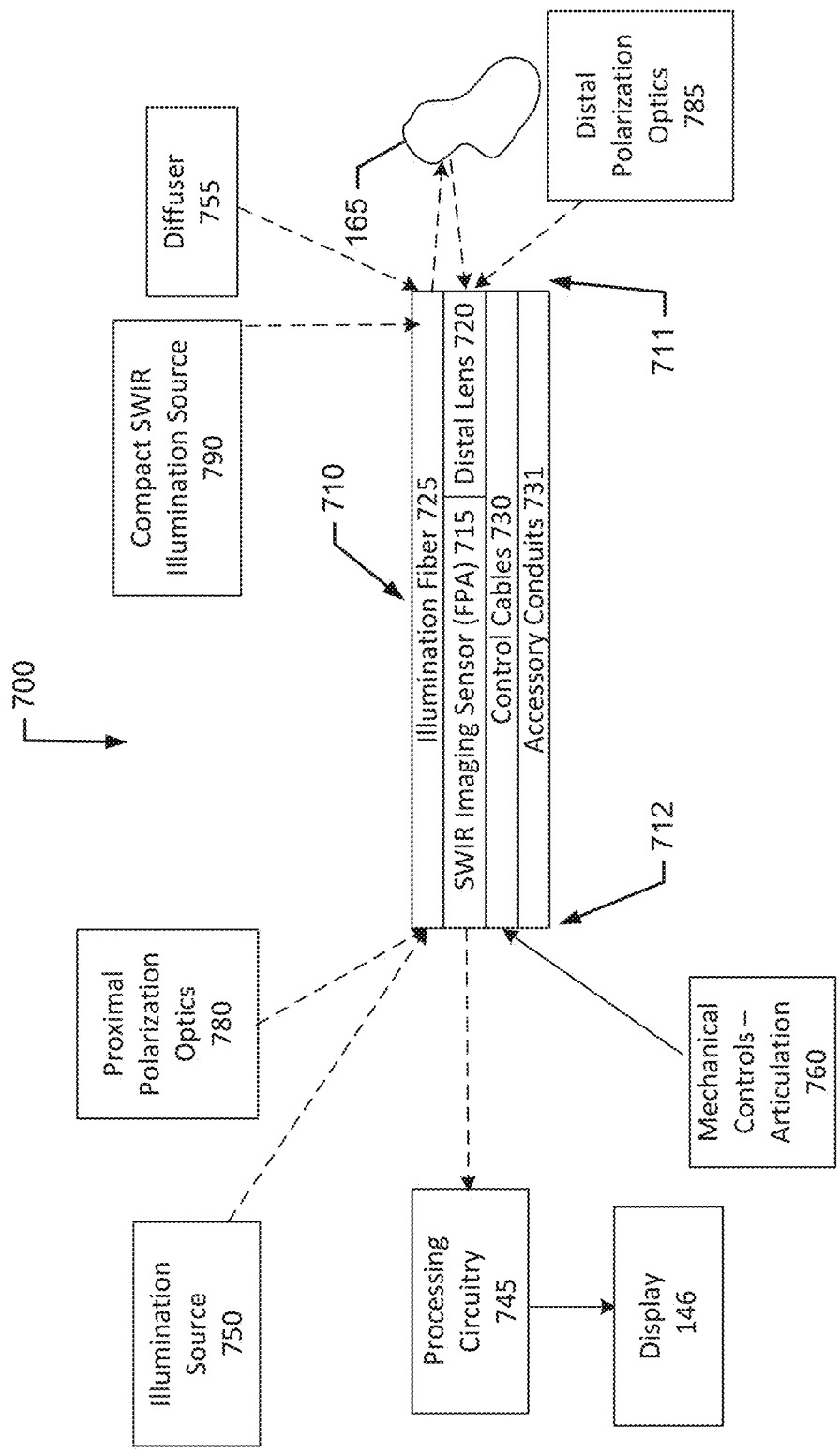
FIG. 7 illustrates a block diagram of another example imaging apparatus according to some example embodiments.

FIG. 7 illustrates a block diagram of another example imaging apparatus according to some example embodiments. The imaging apparatus 700 may be any type of imaging device including, but not limited to, an endoscope, fiberscope, or the like. In this regard, the imaging apparatus 700 or a portion thereof, may be a handheld device with, for example, a handle to permit a user to position and operate the device. The imaging apparatus 700 may be distinguished from imaging apparatus 100 for performing direct imaging, as imaging apparatus 700 may not include a coherent imaging fiber bundle, such as fiber optic bundle 115, and may include, for example, an extremely small SWIR platform at the distal tip 711. The SWIR platform may include, for example, SWIR imaging sensor 715, distal lens 720, and distal polarization optics 785.

The imaging apparatus 700 may include a flexible elongate member 710 that includes a proximal end 712 and a distal end 711. The flexible elongate member 710 may be configured to flex, bend, or otherwise articulate into various positions while supporting optical imaging functionalities. The orientation and positioning of the flexible elongate member 710 may be controllable by a user to position a distal end 711 of the flexible elongate member 710 in a desired position to perform an image capture of an object of interest 165. In this regard, the flexible elongate member 710 may have a distal end 711 which may, when in use, be closer to the object of interest 165 for image capture, and the flexible elongate member 710 may have a proximal end 712, which may be opposite the distal end 711 and may be physically coupled to a handle.

SWIR imaging sensor 715 (e.g., a SWIR sensitive compact imager (Focal Plane Array)) may be included in flexible elongate member 710 or may be operably coupled to distal end 711 of flexible elongate member 710. The SWIR imaging sensor 715 may include a Focal Plane Array (FPA) where the imaging pixels sit in an array. The SWIR imaging sensor 715 may be optically coupled to distal lens 720 (which itself may be part of or coupled to flexible elongate member 710). Distal lens 720 may be an objective lens that images directly onto SWIR imaging sensor 715. Distal lens 720 focuses reflected light from the object of interest 165 back onto the FPA of SWIR imaging sensor 715. Distal lens 720 may be, for example, a gradient index lens (i.e., GRIN lens). Distal lens 720 may have a short focal length and an anti-reflection coating for SWIR. Distal lens 720 may be part of or optically coupled to distal polarization optics 785. The distal polarization optics 785 may condition light reflected off of, for example, object of interest 165 prior to directing light to distal lens 720. In this regard, according to some example embodiments, the distal polarization optics 785 may include lenses shaped to filter, condition, and polarize light energy in the SWIR spectrum reflected off the object of interest 165 for input to the SWIR imaging sensor 715.

When imaging an object up close (sub-inches to inches) the provided illumination can sometimes cause specular reflections off of the object. These specular reflections can overwhelm the image and appear as bright spots in the field of view. When up close, where the object fills the image field, this can limit the ability to see anything, and in particular, fine image details. Using a plurality of polarizers reduces these specular reflections. In one example embodiment, the light source may be initially polarized (e.g., using proximal polarization optics 780) before it illuminates the object and then, the light reflected of the object of interest, may be polarized using a second polarizer or analyzer (e.g., distal polarization optics 785) to control the intensity of the reflected light, especially the polarized specular reflections, that come back into the distal lens 720 and SWIR imaging sensor 715. Proximal polarization optics 780 and distal polarization optics 785 may be adjustable. If the polarization is not desired, for example, the polarizers may be oriented such that they are aligned along the same transmission axis.

SWIR imaging sensor 715 may be a device that is capable of capturing light energy, including light energy in the SWIR spectrum, and converting the received light energy into electrical signals for delivery to processing circuitry (e.g., processing circuitry 745) for image processing to develop a corresponding image. In this regard, the SWIR imaging sensor 715 may be configured to receive imaging light energy at a SWIR wavelength that has been reflected from an object of interest 165 and focused on the SWIR imaging sensor 715 via distal lens 720. According to some example embodiments, the SWIR imaging sensor 715 may be configured to perform imaging at a wide range of wavelengths, which may operate to permit imaging in both the visible spectrum and the SWIR. According to some example embodiments, the SWIR imaging sensor 715 may include an image processor and may be configured to perform some or all image processing local to the SWIR imaging sensor 715. The SWIR imaging sensor 715 may comprise any type of digital camera, sensor array (e.g., charge coupled devices, active pixel sensors, etc.), or the like with sensitivity in the SWIR region of the electromagnetic spectrum. According to some example embodiments, an SWIR imaging sensor 715 that comprises a digital camera may be specifically configured to operate to capture images at the SWIR wavelengths. In some embodiments, SWIR imaging sensor 715 may have a maximum diameter of 0.5 inches. In some embodiments, SWIR imaging sensor 715 may have a resolution of 640× 512 or more and in other embodiments, the SWIR imaging sensor 715 may have a maximum resolution of 320×256 or less, According to some example embodiments, the flexible elongate member 710 may include an illumination fiber 725, or a bundle of illumination fibers. The illumination fiber 725 may be an optical fiber that, in some example embodiments, is disposed within the flexible elongate member 710 and extends from the proximal end 712 of the flexible elongate member 710 to the distal end 711 of the flexible elongate member 710. The illumination fiber 725 may be configured to deliver or guide light energy from an illumination source 750 to the distal end 711 of the flexible elongate member 710 for output into the environment about the distal end 711 of the flexible elongate member 710 to illuminate, for example, an object of interest 165. According to some example embodiments, the illumination fiber 725 may be configured to guide light energy in the SWIR spectrum from the illumination source 750 to the distal end 711 of the flexible elongate member 710. According to some example embodiments, the illumination fiber 725 may be a multi-mode fiber.

While the illumination fiber 725 may be disposed within the flexible elongate member 710, the illumination fiber 725 may be a component of an illumination assembly. According to some example embodiments, the illumination assembly may include the illumination fiber 725, an illumination source 750, and proximal polarization optics 780.

In another embodiment, a compact SWIR illumination source 790 may be placed at the distal tip 711 of the flexible elongate member 710. The compact SWIR illumination source 790 may include or be optically connected to diffuser 755. In this embodiment, the compact SWIR illumination source 790 replaces the functionality of the illumination fiber 725, the proximal polarization optics 780, and the proximal end illumination source 750. In this embodiment, the illumination fiber 725, the proximal polarization optics 780, and the proximal end illumination source 750 may not be included in imaging apparatus 700.

The proximal polarization optics 780 may include one or more lenses configured to condition (e.g. focus) light energy received from an illumination source 750. In this regard, according to some example embodiments, the proximal polarization optics 780 may include lenses shaped to filter, condition, and polarize light energy in the SWIR spectrum from the illumination source 750 for input to the illumination fiber 725.

In some embodiments, illumination source 750 and proximal polarization optics may be housed in the handle coupled to the flexible elongate member 710. Alternatively, in some other embodiments, the functionality of illumination source 750 and proximal polarization optics 780 may be included in a compact SWIR source that is bundled with illumination fiber 725 inside of the flexible elongate member 710.

At distal end 711, illumination fiber 725 may be operably coupled to diffuser 755, which according to some example embodiments, may be static or mechanically moveable or electroactively moveable. Diffuser 755 may be included in or coupled to distal end 711 of flexible elongate member 710. The diffuser 755 may be configured to diffuse or spread the light energy initially generated by the illumination source 750 (and propagated through illumination fiber 725) or compact SWIR illumination source 790 across a surface in a relatively even fashion (e.g., uniformly) to minimize or remove high intensity areas or spots. By diffusing the light energy in this manner, the diffuser 755 may operate to reduce the spatial coherence of the light energy generated by the illumination source 750, thereby reducing speckle in images where the light energy used for illumination originates from the illumination source 750 or to diffuse effects on the light energy caused by propagation through the illumination fiber 725. Further, according to some example embodiments, the diffuser 755 may be a dynamic diffuser that changes (e.g., rotates) or adjusts to dynamically modify the diffusion of the light energy from the illumination source 750.

According to some example embodiments, the imaging apparatus 700 may include or be operably coupled to processing circuitry 745. Processing circuitry 745 may be configured to receive electronic signals corresponding to an image capture of light energy and generate an image. The processing circuitry 745 may be configured to transmit the image to a display 146 (e.g., a liquid crystal display that may be stand-alone, a component of smartphone or tablet, or the like) via wired or wirelessly for viewing by a user for the purpose of analyzing the image, for example, to make a diagnosis, or to navigate the flexible elongate member 710 into a desired position to capture, for example, an image of an object of interest 165. The processing circuitry 745 may include, for example, a processor and a memory, and the processor may be configured to execute instructions, code, or commands stored on the memory to cause the processing circuitry 745 to perform the functionalities of the processing circuitry 745 described herein. Alternatively, or additionally, the processor may be a hardware defined device configured to cause the processing circuitry 745 to perform the functionalities of the processing circuitry 745 describe herein, and may be embodied as, for example, a field programmable gate array (FPGA), an application specific integrated circuit (ASIC), or the like. In some embodiments, processing circuitry 745 may be housed in flexible elongate member 710 or in the handle coupled to flexible elongate member 710. In other embodiments, processing circuitry is included and part of the SWIR imaging sensor 715.

The illumination source 750 may be any type of light generating device that can generate light energy at the SWIR wavelengths for provision to the illumination fiber 725. The illumination source 750 may, according to some example embodiments, be comprised of an incoherent source and filters configured to filter the incoherent light provided by the incoherent source to collectively operate as the illumination source 750. The illumination source 750 may be a laser, a light emitting diode (LED), or the like. According to some example embodiments, the illumination source 750 may be a super-luminescent diode (SLD). In some example embodiments, the illumination source 750 may be coupled directly to the illumination fiber 725. However, in some example embodiments, proximal polarization optics 780 may be employed between the illumination source 750 and the illumination fiber 725.

Additionally, according to some example embodiments, the illumination assembly may also include capabilities to illuminate at wavelengths other than SWIR wavelengths. In this regard, according to some example embodiments, the illumination assembly may include a separate illumination channel for, for example, visible light illumination. In this regard, the illumination assembly may include a visible light source that may be directed through another diffuser to an illumination fiber that guides visible illumination light energy to a distal end of the flexible elongate member 710 to illuminate the object of interest 165 with, for example, visible light.

The flexible elongate member 710 may, according to some example embodiments, include mechanical features that permit the flexible elongate member 710 to bend, flex, contort, or otherwise articulate into a variety of positions. In this regard, according to some example embodiments, the flexible elongate member 710 may include or be disposed within one or more flexible mechanical moldable coils (e.g., gooseneck flexible metal tubing) that permit a user to bend or otherwise articulate the flexible elongate member 710 into a desired position and the flexible elongate member 710 may maintain that desired position. Additionally or alternatively, the flexible elongate member 710 may be mechanically controllable via a control interface to reposition the flexible elongate member 710. In this regard, the imaging apparatus 700 may include mechanical controls 760 that may be operably coupled to control cables 730 (e.g., wires) that are disposed within the flexible elongate member 710. For example, the control cables 730 may be affixed to an inner surface of an external sheath of the flexible elongate member 710 and may be movable to reposition the flexible elongate member 710. In this regard, the mechanical controls 760 may include a user interface in the form of a joystick or other type of directional controls that may be physically connected to the control cables 730 such that, movement of the mechanical controls 760 causes movement of the control cables 730 in the flexible elongate member 710 to position (e.g., bend or otherwise articulate) the flexible elongate member 710. According to some example embodiments, the control cables 730 may be affixed in a manner such that the directional controls operate to maneuver a portion near the distal end 711 (e.g., a tip) of the flexible elongate member 710. According to some example embodiments, the directional controls may electrically connected to electromechanical actuators (e.g., servos or the like) that receive electrical signals from the directional controls and cause the electromechanical actuators to move thereby causing the control cables 730 that are connected to the electromechanical actuators to move and position the flexible elongate member 710.

Additionally, according to some example embodiments, the flexible elongate member 710 may also include one or more accessory conduits 731. In regard, according to some example embodiments, an accessory conduit 731 may be an open tube in the flexible elongate member 710 that would permit a user to guide an item from the proximal end 712 of the flexible elongate member 710 to the distal end 711 of the flexible elongate member 710. For example, an accessory conduit 731 may be configured to permit a tool (i.e., a pincer, cutting tool, cauterizing tool, or the like) to be inserted into a proximal end of the accessory conduit 731 and pushed through the accessory conduit 731 to extend out of the distal end 711 of the accessory conduit 731 and the distal end 711 of the flexible elongate member 710. In this manner, a user may be capable of performing actions at the distal end 711 of the flexible elongate member 710 while visualizing the environment at the distal end 711 of the flexible elongate member 710 via the display 146. Additionally or alternatively, an accessory conduit 731 may be configured to guide fluids (e.g., water) or gases (e.g., air) into a space at the distal end 711 of the flexible elongate member 710 as required for certain applications of the imaging apparatus 700.

Figure 8:
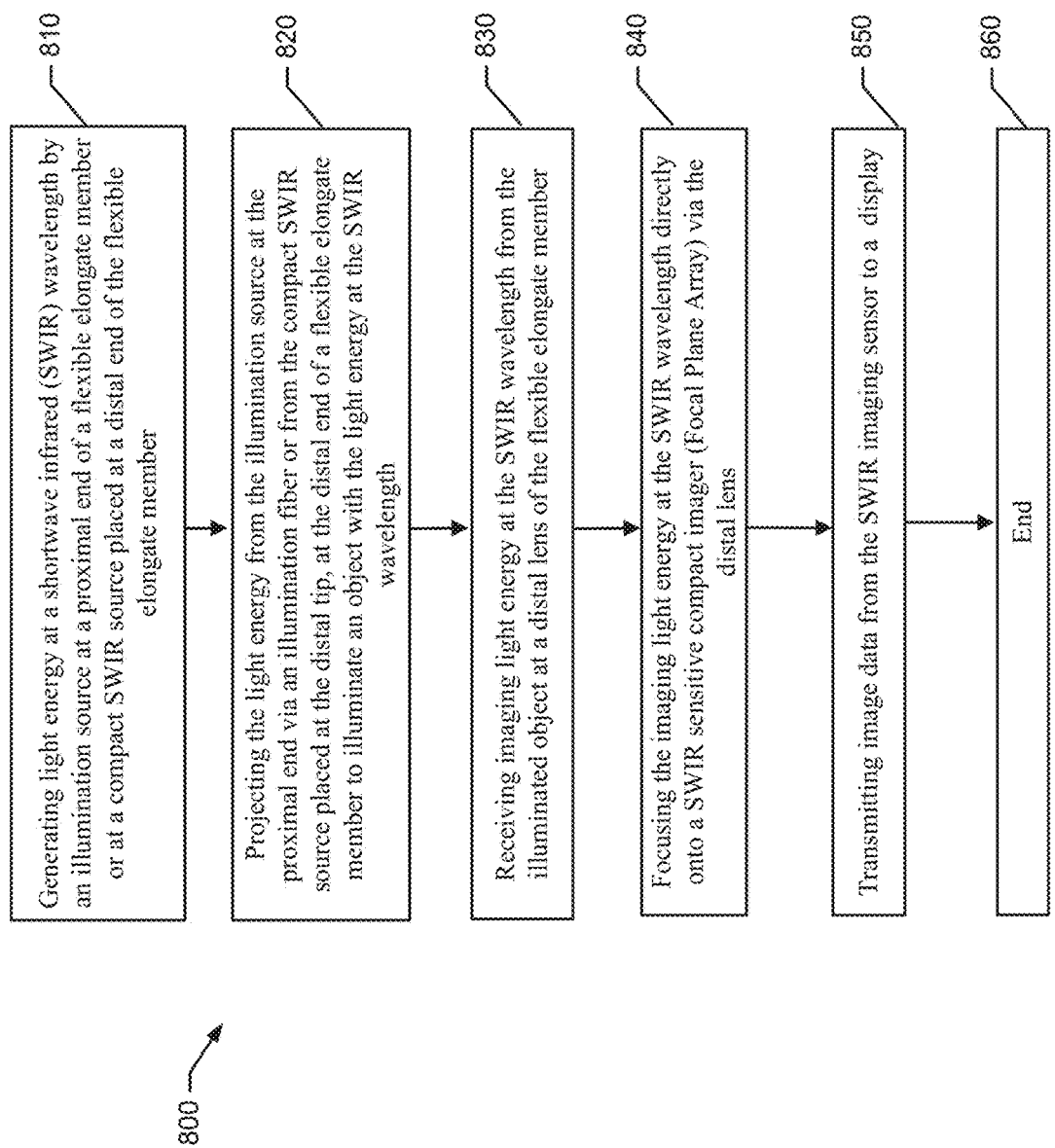
FIG. 8 illustrates a block diagram of another example method for imaging according to various example embodiments.

FIG. 8 illustrates a block diagram of an example method 800 for imaging according to various example embodiments. In accordance with the description above, according to some example embodiments, the example method 800 may include, at 810, generating light energy, using a laser, LED, or the like, at a shortwave infrared (SWIR) wavelength by an illumination source at a proximal end of a flexible elongate member or at a compact SWIR source at a distal tip of the elongate member.

From 810, flow may move to 820, which includes guiding the light energy from the illumination source at the proximal end, via an illumination fiber, or from the compact SWIR source placed at the distal tip, to a distal end of a flexible elongate member to illuminate an object with the light energy at the SWIR wavelength. In some embodiments, the light energy at the SWIR wavelength is passed through a diffuser coupled to the distal end of the flexible elongate member prior to illuminating the object.

From 820, flow may move to 830, which includes receiving imaging light energy at the SWIR wavelength from the illuminated object at a distal lens of the flexible elongate member. In this regard, the imaging light energy may be light energy at the SWIR wavelength originally from the illumination source at the proximal end or from the compact SWIR source placed at the distal tip which is reflected off of the object.

From 830, flow may move to 840, where the imaging light energy at the SWIR wavelength is focused directly onto a SWIR sensitive compact imager (Focal Plane Array) via a distal lens.

From 840, flow may move to 850, which includes transmitting image data (e.g., the electrical output signal), via wired or wireless, that is representative of the image itself from the SWIR imaging sensor through the flexible elongate member to a display. This may include transmitting the image data to an image processor and processing the images prior to sending to a display. The display may be a standalone display unit such as a smartphone, tablet, or other portable computing and display device. From 850, flow may move to 860 and end. Additionally or alternatively, the example method 800 may include adding a fluorescent dye to the object that reflects light energy at the SWIR wavelength.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. An imaging apparatus comprising:
    a flexible elongate member having a distal end and proximal end, the flexible elongate member comprising:
        a shortwave infrared (SWIR) imaging sensor configured for wavelengths from 1.0 micrometer to 1.7 micrometers;
        a distal lens optically coupled to the SWIR imaging sensor and disposed at the distal end of the flexible elongate member, the distal lens configured to focus light energy at a SWIR wavelength onto the SWIR imaging sensor;
        a compact SWIR illumination source disposed entirely at the distal end of the flexible elongate member and configured to provide light energy at the SWIR wavelength at the distal end of the flexible elongate member for output to illuminate an object, wherein the light energy at the SWIR wavelength is not guided from the proximal end to the distal end of the flexible elongate member, wherein the imaging apparatus does not include illumination fiber that directs light energy at the SWIR wavelength from the proximal end to the distal end of the flexible elongate member; and
        one or more control cables disposed within the flexible elongate member enabling movement of the flexible elongate member; and
    a handle coupled to the flexible elongate member; and
    mechanical controls operably coupled to the control cables for directing the flexible elongate member and focusing capabilities for imaging.

2. The imaging apparatus of claim 1, wherein the flexible elongate member further comprises a dynamic diffuser configured to dynamically modify spatial coherence of the light energy generated by the illumination source to enhance resolution of an image.

3. The imaging apparatus of claim 1, wherein the flexible elongate member further comprises:
    a first polarization optic optically coupled to the illumination source, wherein the first polarization optic polarizes the light energy at the SWIR wavelength; and
    a second polarization optic optically coupled to the distal lens, wherein the second polarization optic is adjustable to control an intensity of the light energy at the SWIR wavelength reflected off of the object.

4. The imaging apparatus of claim 1, wherein the SWIR imaging sensor has a resolution of 640×512 and a maximum diameter of 0.5 inches.

5. The imaging apparatus of claim 1, wherein the imaging apparatus is an endoscope and the distal end further comprises a micro stepper motor, a lead screw, and a lens holder to increase resolution of an image.

6. An imaging apparatus comprising:
a distal end;
a proximal end;
a shortwave infrared (SWIR) imaging sensor disposed at the distal end and configured to detect wavelengths from 1.0 micrometer to 1.7 micrometers;
a lens disposed on the distal end, the lens configured to focus light energy at a SWIR wavelength on the SWIR imaging sensor;
SWIR anti-reflective coating disposed on the lens; and
a compact SWIR illumination source disposed entirely at the distal end and configured to output illumination at the SWIR wavelength adjacent to the distal end toward an object, wherein the SWIR imaging sensor is configured to receive imaging light energy at the SWIR wavelength reflected from the object and focused through the lens, wherein the light energy at the SWIR wavelength is not guided from the proximal end to the distal end, wherein the imaging apparatus does not include illumination fiber from the proximal end to the distal end.

7. The imaging apparatus of claim 6, wherein the illuminator comprises an illumination source configured to provide light energy at the SWIR wavelength, the illumination source being a super-luminescent diode.

8. The imaging apparatus of claim 6, wherein the SWIR imaging sensor has a resolution of 640×512 and a maximum diameter of 0.5 inches.

9. The imaging apparatus of claim 6 further comprising:
a first polarization optic optically coupled to the illuminator, wherein the first polarization optic polarizes light energy at the SWIR wavelength; and
a second polarization optic optically coupled to the lens, wherein the second polarization optic is adjustable to control intensity of the light energy at the SWIR wavelength reflected off of the object.

10. A method comprising:
generating light energy at a shortwave infrared (SWIR) wavelength by a compact SWIR illumination source disposed entirely at a distal end of a flexible elongate member, wherein the light energy at the SWIR wavelength has a wavelength between 1.0 micrometer to 1.7 micrometers, wherein the light energy is not guided from a proximal end of the flexible elongate member to the distal end of the flexible elongate member;
projecting the light energy from the distal end of the flexible elongate member to illuminate an object with the light energy at the SWIR wavelength;
receiving imaging light energy at the SWIR wavelength reflected from the illuminated object at a distal lens of the flexible elongate member;
focusing the imaging light energy at the SWIR wavelength onto a SWIR sensitive compact imager via the distal lens; and
transmitting image data from the SWIR imaging sensor to a display.

11. The method of claim 10, further comprising passing the light energy generated by the illumination source through a dynamic diffuser prior to illuminating the object to reduce spatial coherence of the light energy generated by the illumination source.

12. The method of claim 10, further comprising:
polarizing the light energy generated by the illumination source with a first polarization optic;
polarizing the imaging light energy from the illuminated object with a second polarization optic; and
removing specular reflections in the imaging light energy from the illuminated object by adjusting the first polarization optic and the second polarization optic.

13. The method of claim 10 further comprising adding a fluorescent dye to or near the object, the fluorescent dye being configured to emit light energy at the SWIR wavelength.

14. The method of claim 10 further comprising performing image processing on signals corresponding to the imaging light energy at the SWIR wavelength received at the SWIR sensitive compact imager to generate an image of the object.

* * * * *